United States Patent [19]

Morris et al.

[11] Patent Number: 5,519,042

[45] Date of Patent: May 21, 1996

[54] METHOD OF TREATING HYPERPROLIFERATIVE VASCULAR DISEASE

[75] Inventors: Randall E. Morris, Stanford, Calif.; Robert R. Bartlett, Darmstadt, Germany

[73] Assignee: Hoechst Aktiengesellschaft, Frankfurt am Main, Germany

[21] Appl. No.: 181,116

[22] Filed: Jan. 13, 1994

[51] Int. Cl.$^6$ .......................... A61K 31/42; A61K 31/36
[52] U.S. Cl. ..................... 514/378; 514/466; 514/824
[58] Field of Search .................................. 514/378, 521, 514/824, 18, 458, 763, 466

[56] References Cited

U.S. PATENT DOCUMENTS 4,061,767  12/1977  Ertel et al. .............................. 514/466

FOREIGN PATENT DOCUMENTS

| 0013376B1 | 7/1980 | European Pat. Off. . |
| 0217206B1 | 4/1987 | European Pat. Off. . |
| 0484223A2 | 5/1992 | European Pat. Off. . |
| 0538783A1 | 4/1993 | European Pat. Off. . |
| 0551182A1 | 7/1993 | European Pat. Off. . |
| 0607775A2 | 7/1994 | European Pat. Off. . |
| WO91/16892 | 11/1991 | WIPO . |
| WO95/19169 | 7/1995 | WIPO . |

OTHER PUBLICATIONS

The Merck Index, 10th Edition, p. 396, abstract No. 2748. (1983).
Herrman et al., Pharmacological Approaches to the Prevention of Restenosis Following Angioplasty. The Search for the Holy Grail? (Part II): Drugs; 1993; (Abstract).
Grinstead et al.; Amiprilose in the Prevention of Restenosis After Coronary Intervention in a Swine Model; Coron. Artery Dis.; 1993 (Abstract).
Stone et al.; A Randomized Trial of Corticosteroids for the Prevention of Restenosis in 102 Patients Undergoing Repeat Coronary Agioplasty; Catheter. Cardiovasc. Diagn.; 1989 (Abstract).
Pepine et al.; A Controlled Trial of Cortiscosteroids to Prevent Restenosis After Coronary Angioplasty; Circulation; 1990 (Abstract).
Muller et al.; Site–Specific Dexamethasone Delivery for the Prevention of Neointimal Thickening After Vascular Stent Implantation; Coron. Artery Dis.; 1994 (Abstract).
Karas et al.; Restenosis Following Coronary Angioplasty; Clin. Cardiol.; 1991 (Abstract).
MacDonald et al., Effects of Leflunomide and Cyclosporine on Aortic Allograft Chronic Rejection in the Rat, Transplantation Proceedings, vol. 26, No. 6, pp. 3244–3245 (Dec. 1994).
Mattar et al., Inhbition of the Epidermal Growth Factor Receptor Tyrosine Kinase Activity by Leflunomide, FEBS 13234, vol. 334, No. 2, pp. 161–164 (Nov. 1993).
Williams et al., Immunosuppressive Effects of Leflunomide in a Cardiac Allograft Model, Transplantation Proceedings, vol. 25, No. 1, pp. 745–746 (Feb. 1993).
Bartlett et al., Leflunomide (HWA 486), A Novel Immunomodulating Compound For The Treatment of Autoimmmune Disorders and Reactions Leading to Transplantation Rejection, Agents and Actions, vol. 32, 1/2, pp. 10–21 (1991).
Bilder et al., Tyrphostins Inhibit PDGF–Induced DNA Synthesis and Associated Early Events in Smooth Muscle Cells, American Journal of Physiology, vol. 260, No. 4, pp. C721–C730, (Apr. 1991).
Cao et al., Leflunomide, A New Immunosuppressant, Inhibits Trosine Kinase, Calcium Signaling and DNA Sythesis in Vascular Smooth Muscle Cells, The FASEB Journal, Transplantation: Tolerance and Rejection 2812, vol. 8, No. 4, (Mar. 1994).
Foegh et al., Molecular Biology of Intimal Proliferation, Current Opinion in Cardiology, vol. 8, No. 6 pp. 938–950, (Nov. 1993).
Gregory et al., Leflunomide is a New Immunosuppressant that Effectively Reduced Arterial Intimal Thickening Produced by Alloimmune Injury, The Journal of Heart and Lung Transplantation, vol. 13, No. 1, Part. 2, p. S68, Abstract No. 145, (Jan./Feb. 1994).

*Primary Examiner*—Marianne M. Cintins
*Assistant Examiner*—Kevin E. Weddington
*Attorney, Agent, or Firm*—Finnegan, Henderson, Farabow, Garrett & Dunner

[57] ABSTRACT

A method of preventing or treating hyperproliferative vascular disease in a mammal consists of administering to a mammal an effective amount of carboxyamide compounds.

9 Claims, No Drawings

METHOD OF TREATING HYPERPROLIFERATIVE VASCULAR DISEASE

DESCRIPTION

European Patent 13,376 discloses N-(4-trifluoromethylphenyl)-5-methylisoxazole- 4-carboxamide (compound 1) as being anti-inflammatory. Processes for the preparation of this compound are also described therein.

It is additionally known that the compound 1 and N-(4-trifluoromethylphenyl)-2-cyano- 3-hydroxycrotonamide (compound 2) have immunomodulation properties, so that they are suitable as pharmaceutical against chronic graft versus host diseases and against autoimmune disorders, in particular systemic Lupus erythematosus (EP 0,217,206), U.S. Pat. No. 4,061,767 describes the use of 2-hydroxyethylidenecyanoacetanilide derivatives for the preparation of pharmaceuticals having anti-inflammatory and analgesic action.

Many individuals suffer from vascular disease caused by a partial blockage of the blood vessels that supply the tissue with nutrients. More severe blockage of blood vessels in such individuals often leads to hypertension, ischemic injury, stroke, or myocardial infarction. Typically vascular occlusion is preceded by vascular stenosis resulting from intimal smooth muscle cell hyperplasia. The underlying cause of the intimal smooth muscle cell hyperplasia is vascular smooth muscle injury and disruption of the integrity of the endothelial lining. The overall disease process can be termed a hyperproliferative vascular disease because of the etiology of the disease process. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor (PDGF), epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles.

Vascular injury causing intimal thickening can be broadly categorized as being either biologically or mechanically induced. Both biologically and mechanically mediated vascular injury lead to stenosis, and migration and proliferation of vascular smooth muscle plays a crucial role in the pathogenesis of consecutive atherosclerosis. Atherosclerotic lesions include massive accumulation of lipid laden "foam cells" derived from monocyte/macrophage and smooth muscle cells. Formation of "foam cell" regions is associated with a breech of endothelial integrity and basal lamina destruction. Triggered by these events, restenosis is produced by a rapid and selective proliferation of vascular smooth muscle cells with increased new basal lamina (extracellular matrix) formation and results in eventual blocking of arterial pathways.

Mechanical injuries leading to intimal thickening result following balloon angioplasty, vascular surgery, transplantation surgery, and other similar invasive processes that disrupt vascular integrity. Intimal thickening following balloon catheter injury has been studied in animals as a model for arterial restenosis that occurs in human patients following balloon angioplasty. It has been shown that deendothelilization with an intraarterial catheter that dilates an artery injures the innermost layers of medial smooth muscle and may even kill some of the innermost cells. Injury is followed by platelet aggregation, release of PDGF, and proliferation of the medial smooth muscle cells, after which many of them migrate into the intima through fenestrae in the internal elastic lamina and proliferate to form a neointimal lesion.

Vascular stenosis can be detected and evaluated using angiographic or sonographic imaging techniques and is often treated by percutaneous transluminal coronary angioplasty (balloon catheterization). Within a few months following angioplasty, however, the blood flow is reduced in approximately 30– 40 percent of these patients as a result of restenosis caused by a response to mechanical vascular injury suffered during the angioplasty procedure, as described above.

In an attempt to develop better agents for preventing or reducing smooth muscle proliferation and intimal thickening, the use of the balloon catheter induced arterial injury in a variety of mammals has been developed as a standard model of vascular injury that will lead to intimal thickening and eventual vascular narrowing.

Surprisingly a compound of the formula I or II shows an effective inhibition of intimal thickening in injured carotid arteries.

Therefore the invention relates to a method of preventing or treating hyperproliferative vascular disease in a mammal in need thereof by administering an amount, effective to inhibit intimal thickening in said mammal, of a compound of the formula I or II

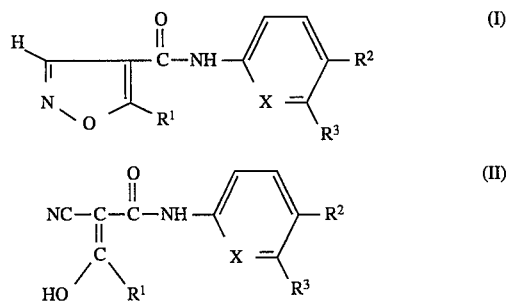

wherein
R$^1$ denotes
  a) methyl,
  b) (C$_3$–C$_6$)-cycloalkyl,
  c) (C$_2$–C$_6$)-alkyl, having at least 1 triple or double bond between the carbon atoms,
R$^2$ denotes
  a) —CF$_3$ or
  b) —CN,
R$^3$ denotes
  a) (C$_1$–C$_4$)-alkyl or
  b) hydrogen atom,
X denotes
  a) —CH— group or
  b) nitrogen atom,
the compound of the formula II being present as such or in the form of a physiologically tolerable salt.

Preferred are compounds of the formula I or II wherein
R$^1$ denotes a) methyl,
b) cyclopropyl or
c) —CH$_2$—CH$_2$—C≡CH, R$^2$ denotes —CF$_3$, R$^3$ denotes methyl or hydrogen atom and X denotes —CH— group.

Especially preferred is a compound of the formula I or II, wherein R$^1$ denotes methyl, R$^2$ denotes —CF$_3$, R$^3$ denotes hydrogen atom and X denotes —CH— group.

Suitable physiologically tolerable salts of the compound of the formula II are, for example, alkali metal, alkaline earth metal or ammonium salts, including those of physiologically tolerable organic ammonium bases.

The compounds of the formula I or II can be prepared by the following process:

A compound of the formula III

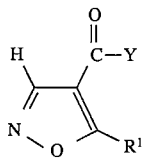

in which Y represents a halogen atom, preferably chlorine or bromine, is reacted with the amine of the formula (IV)

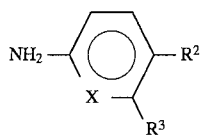

wherein R$^2$, R$^3$ and X have the same meanings as in formula I, to give the compound of the formula I, and this can then be reacted in the presence of a basic agent to give the compound of the formula II.

The starting substances for the reactions are known or can be easily prepared by methods known from the literature. The above-mentioned reactions are carried out under standard conditions in a known manner (EP 13,376; EP 484,223; EP 538,783; U.S. Pat. No. 4,061,767).

The invention also relates to pharmaceuticals which contain an effective amount of compound of the formula I and/or compound of the formula II, the compound of the formula II being present as such or in the form of a physiologically tolerable salt, in addition to pharmaceutically suitable and physiologically tolerable excipients, diluents and/or other active substances and auxiliaries.

The invention also relates to a process for the preparation of a pharmaceutical for the treatment of hyperproliferative vascular disease, which comprises bringing a compound of the formula I or II or a physiologically tolerable salt of compound of the formula II or a mixture thereof into a suitable administration form using a pharmaceutically suitable and physiologically acceptable excipient and, if appropriate, other suitable active substances, additives or auxiliaries.

The pharmaceutical according to the invention can be administered orally, intravascularly, topically, rectally, parenterally, intranasally, intrabronchially, transdermally or via a vascular stent impregnated with a compound of the formula I or II. Administration is carried out before, during and/or after a biologically or mechanically mediated vascular injury, or under conditions that would predispose a mammal to suffering such a vascular injury.

Suitable solid or liquid pharmaceutical administration forms are, for example, granules, powders, coated tablets, tablets, (micro)capsules, suppositories, syrups, juices, suspensions, emulsions, drops or injectable solutions and preparations having a protracted release of active substance, within these preparations customary auxiliaries, such as excipients, disintegrants, binders, coating agents, swelling agents, lubricants, flavorings, sweeteners or solubilizers are used. Commonly used auxiliaries are, for example, magnesium carbonate, titanium dioxide, lactose, mannitol and other sugars, talc, milk protein, gelatin, starch, cellulose and its derivatives, animal and vegetable oils, polyethylene glycols and solvents, such as, for example, sterile water and mono- or polyhydric alcohols, for example glycerol.

Preferably, the pharmaceutical preparations are prepared and administered in dosage units, each unit containing as the active constituent a certain dose of compound of the formula I and/or II, where compound of the formula II is present as such or in the form of a physiologically tolerable salt. In the case of solid dosage units, such as tablets, capsules or suppositories, this dose can be up to about 500 mg, preferably 5 to 400 mg, more preferably 5 to 200 mg, in particular 10 to 100 mg, and especially 10 to 25 mg.

For the treatment of a patient (70 kg) suffering from a hyperproliferative vascular disease in the early phases an intravenous infusion treatment of at most 1200 mg per day and in the later rehabilitation phases an oral administration of 3 times 300 mg per day of compound of the formula I and/or II and/or of the corresponding salts of compound of the formula II are indicated.

Under certain circumstances, however, higher or lower doses may also be appropriate. The administration of the dose can be carried out both by singly administration in the form of an individual dosage unit or else several smaller dosage units and by multiple administration of subdivided doses at specific intervals.

A compound of the formula I or II and/or its corresponding salts can also be combined during the preparation of the above-mentioned pharmaceutical administration forms together with other immunosuppressive substances, for example rapamycin (Wyeth-Ayerst Inc., Princeton, N.J.), mycophenolic acid (Sigma Chemical Co., St. Louis, Mo.), cyclosporin A (Sandoz Inc., East Hannover, N.J.), FK506 (Fujisawa Inc., Osaka, Japan) or brequinar sodium.

As such, the compound of the formula I or II is useful, alone or in combination with other pharmacological effective substances, in preventing or treating intimal smooth muscle cell hyperplasia, restenosis, and vascular occlusion in a mammal, particularly following either biologically or mechanically mediated vascular injury, or under conditions that would predispose a mammal to suffering such a vascular injury. Biologically mediated vascular injury includes, but is not limited to injury due to thrombotic events; autoimmune and alloimmune related disorders; infectious disorders including endotoxins and herpes viruses, such as cytomegalovirus, mediated disorders; metabolic disorders such as atherosclerosis; and vascular injury resulting from hypothermia and irradiation. Mechanically mediated vascular injury includes, but is not limited to vascular injury caused by catheterization procedures or vascular scraping procedures such as percutaneous transluminal coronary angioplasty; vascular surgery; transplantation surgery; laser treatment, and other invasive procedures which disrupt the integrity of the vascular intima or endothelium.

Preventing includes the prophylactic prevention of hyperproliferative vascular disease in a susceptible mammal and treating includes arresting the development, and retarding the progression of hyperproliferative vascular disease in a susceptible mammal.

EXAMPLE 1

Pharmacological Tests and Results

The effect of N-(4-trifluoromethylphenyl)-5-methylisoxazole-carboxamide (compound I) on hyperproliferative vascular disease was established in an in vivo standard pharmacological test procedure that emulates the hyperproliferative effects observed in mammals that are undergoing intimal smooth muscle proliferation and are therefore developing restenosis. Cyclosporin A was also evaluated in these test procedure for the purpose of comparison.

Compound 1 was also evaluated in an in vivo standard pharmacological test procedure that emulates the vascular injury suffered and restenosis that develops following percutaneous transluminal coronary angioplasty in humans.

Intimal smooth muscle proliferation was produced by balloon catheter injury to the left carotid artery of groups of 6, male Sprague-Dawley (SD) rats. Endothelial denudation and vascular injury were achieved in the left carotid arteries of male Sprague-Dawley rats. A balloon catheter (2 French Fogarty, Edwards Laboratories, Santa Anna, Calif.) was passed through the external carotid artery into the aorta. The balloon was then inflated with an amount of water sufficient to distend the common carotid artery and was then pulled back to the external carotid artery. The inflation and pull back were repeated three times. This procedure leads to complete denudation of the endothelium throughout the common carotid artery, and also some injury typically occurs to the medial smooth muscle cells.

During a 17-days period (3 days before operation to 13 days after operation), these rats were divided into 2 groups of 6 animals and treated daily with compound 1 (20 mg/kg/day, intraperitoneal (i.p.)) or cyclosporin A (3 mg/kg/day; i.p.).

An injured group not treated with any drug was used as an injured control to establish the amount of intimal thickening in the absence of treatment. The right carotid was used as an uninjured control in all groups.

After the 14 day post-operative period, the rats were sacrificed, the carotids removed. The mean areas of the intima, media and total blood vessel wall were measured by morphometry. The injured artery was also examined using histopathologic assays. Results are presented as an intima percent, expressed as follows:

$$\frac{\text{area of intima}}{\text{area of intima} + \text{area of media}} * 100$$

The following table shows the data obtained in the above experiment.

Effect of test substances on intimal thickening in injured carotid arteries

| Test Group | Intima Percent (±S.E.)*) |
| --- | --- |
| Uninjured Control | 0.00 ± 0.00 |
| Untreated Injured Control | 46.06 ± 16.36 |
| Compound 1 (20 mg/kg) | 7.88 ± 7.88 |
| CsA*) (3 mg/kg - 14 days) | 39.39 ± 26.06 |

*)S.E. = standard error, CsA = cyclosporin A.

These results show that treatment with compound 1 resulted in an 83% decrease in the mean percentage intimal thickening compared with the untreated injured control group. Cyclosporin A failed to produce any meaningful reduction in intimal thickening.

The results of the in vivo standard test procedure demonstrate that compound 1 is useful in preventing or treating hyperproliferative vascular disease. Specifically, compound 1 is useful in preventing or treating intimal smooth muscle cell hyperplasia, restenosis, and vascular occlusion in a mammal, particularly following either biologically or mechanically mediated vascular injury, or under conditions that would predispose a mammal to suffering such a vascular injury.

EXAMPLE 2

Preparation of N-(4-trifluoromethylphenyl)-5-methylisoxazole-4-carboxamide (Compound 1)

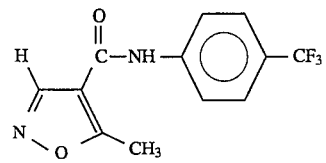

A solution of 0.05 mol of 5-methylisoxazole-4-carbonyl chloride (7.3 g) in 20 ml of acetonitrile is added drop wise at room temperature to a solution of 0.1 mol of 4-trifluoromethylaniline (16.1 g) in 150 ml of acetonitrile. After stirring for 20 minutes, the precipitated 4-trifluoromethylaniline hydrochloride is filtered off with suction and washed twice with 20 ml of acetonitrile each time, and the combined filtrates are concentrated under reduced pressure. The yield is 12.8 g of white, crystalline N-(4-trifluoromethylphenyl)-5-methylisoxazole-4-carboxamide (compound 1). Melting point from toluol 166,5° C.

EXAMPLE 3

Preparation of N-(4-trifluoromethylphenyl)-2-cyano-3-hydroxycrotonamide (compound 2)

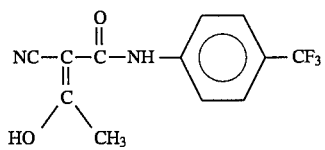

0.1 mol of N-(4-trifluoromethylphenyl)-5-methylisoxazole-4-carboxamide is dissolved in 100 ml of methanol and treated at +10° C. with a solution of 0.11 mol (4.4 g) of sodium hydroxide in 100 ml of water. The mixture is stirred for 30 minutes and, after diluting with water, is acidified with concentrated hydrochloric acid. The precipitated crop of crystals is filtered off with suction, washed with water and dried in air. The yield is 24.4 g of N-(4-trifluoromethylphenyl)-2-cyano-3-hydroxycrotonamide (compound 2). Melting point from methanol 205° to 206° C.

EXAMPLE 4

Acute Toxicity after Intraperitoneal Administration

The acute toxicity after intraperitoneal administration of the test substances was determined with NMRI mice (20 to 25 g) and SD rats (120 to 195 g). The test substance was suspended in a 1% strength sodium carboxymethylcellulose solution. The different dosages of the test substance were administered to the mice in a volume of 10 ml/kg of body weight and to the rats in a volume of 5 ml/kg of body weight. Per dosage, 10 animals were used. After 3 weeks, the acute toxicity was determined by the method of Litchfield and Wilcox. The results are summarized in the table 2.

TABLE 2

|  | Compound 1 acute toxicity intraperitoneal $LD_{50}$ (mg/kg) | Compound 2 acute toxicity intraperitoneal $LD_{50}$ (mg/kg) |
| --- | --- | --- |
| NMRI mouse | 185 (163–210) | 150 (100–200) |
| SD rat | 170 (153–189) |  |

We claim:

1. A method of preventing or treating hyperproliferative vascular disease in a mammal in need thereof, comprising administering an amount, effective to inhibit intimal thickening in said mammal, of a compound of the formula I or II

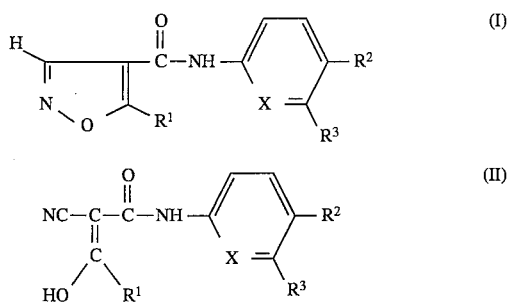

wherein $R^1$ denotes
   a) methyl,
   b) $(C_3-C_6)$-cycloalkyl or
   c) $(C_2-C_6)$-alkyl, having at least 1 double or triple bond between the carbon atoms, $R^2$ denotes
   a) —$CF_3$ or
   b) —CN, $R^3$ denotes
   a) $(C_1-C_4)$- alkyl or
   b) hydrogen atom, X denotes
   a) —CH-group or
   b) nitrogen atom, or a physiologically tolerable salt of a compound of formula II.

2. The method of claim 1, wherein
   $R^1$ denotes
      a) methyl,
      b) cyclopropyl or
      c) —$CH_2$—$CH_2$—C≡CH,
   $R^2$ denotes —$CF_3$,
   $R^3$ denotes methyl or hydrogen atom and
   X denotes —CH— group.

3. The method of claim 1, wherein the compound of the formula I or II is selected from the group consisting of N-(4-trifluoromethylphenyl)-2-cyano-3-hydroxycrotonamide and N-(4-trifluoromethylphenyl)-5-methylisoxazole-4-carboxamide.

4. The method of claim 1, wherein the administering is accomplished orally, parenterally, intravascularly, intranasally, intrabronchially, transdermally, rectally, or via a vascular stent impregnated with a compound of the formula I or II.

5. The method of claim 1, wherein the compound of the formula I or II is administered concurrent with said mammal undergoing a percutaneous transluminal coronary angioplasty procedure.

6. The method of claim 5, which further comprises administering the compound of the formula I or II subsequent to said mammal undergoing a percutaneous transluminal coronary angioplasty procedure.

7. The method of claim 1, wherein the hyperproliferative vascular disease is selected from the group consisting of intimal smooth muscle cell hyperplasia, restenosis, and vascular occlusion.

8. The method of claim 1, wherein the compound of the formula I or II is administered prior to, concurrent with or subsequent to said mammal sustaining a biologically mediated vascular injury.

9. The method of claim 1, wherein a compound of the formula I or II is administered prior to, concurrent with or subsequent to said mammal sustaining a mechanically mediated vascular injury.

* * * * *